United States Patent
Hruza

(10) Patent No.: US 10,426,865 B2
(45) Date of Patent: Oct. 1, 2019

(54) ABSORBENT PAD THAT INCLUDES A FATTY ACID COMPOSITION FOR ODOR CONTROL

(71) Applicant: BioNutraTech, Inc., Houston, TX (US)

(72) Inventor: Sandra L. Hruza, Houston, TX (US)

(73) Assignee: BioNutraTech, Inc., Houston, TX (US)

( * ) Notice: Subject to any disclaimer, the term of this patent is extended or adjusted under 35 U.S.C. 154(b) by 369 days.

(21) Appl. No.: 15/380,496

(22) Filed: Dec. 15, 2016

(65) Prior Publication Data

US 2017/0173207 A1 Jun. 22, 2017

Related U.S. Application Data

(60) Provisional application No. 62/269,282, filed on Dec. 18, 2015.

(51) Int. Cl.
| | | |
|---|---|---|
| A61L 15/46 | (2006.01) |
| A61L 15/60 | (2006.01) |
| A61L 15/28 | (2006.01) |
| A61L 15/20 | (2006.01) |
| A61F 13/535 | (2006.01) |
| A61F 13/539 | (2006.01) |
| A61F 13/84 | (2006.01) |
| A61L 15/18 | (2006.01) |
| A61F 13/53 | (2006.01) |

(52) U.S. Cl.
CPC ............ *A61L 15/46* (2013.01); *A61F 13/535* (2013.01); *A61F 13/539* (2013.01); *A61F 13/8405* (2013.01); *A61L 15/18* (2013.01); *A61L 15/20* (2013.01); *A61L 15/28* (2013.01); *A61L 15/60* (2013.01); *A61F 2013/530343* (2013.01); *A61F 2013/530496* (2013.01); *A61F 2013/53908* (2013.01); *A61F 2013/8408* (2013.01)

(58) Field of Classification Search
CPC ........... A61L 15/46; A61L 15/18; A61L 15/20; A61L 15/28; A61L 15/60; A61F 13/535; A61F 13/539; A61F 13/8405
See application file for complete search history.

(56) References Cited

U.S. PATENT DOCUMENTS

| | | |
|---|---|---|
| 5,443,845 A | 8/1995 | Felix |
| 5,725,885 A | 3/1998 | Felix et al. |
| 5,954,868 A | 9/1999 | Felix et al. |
| 6,277,279 B1 | 8/2001 | Hruza |
| 7,393,521 B2 | 7/2008 | Hruza |
| 7,799,360 B2 | 9/2010 | Ronning et al. |
| 8,916,047 B2 | 12/2014 | Hruza |
| 2004/0166248 A1* | 8/2004 | Hu .......................... B01J 2/006 427/553 |
| 2004/0241254 A1* | 12/2004 | Kopas .................... A61K 8/922 424/727 |
| 2011/0160688 A1* | 6/2011 | Warren ............... A61F 13/8405 604/367 |
| 2012/0012526 A1* | 1/2012 | Hruza ...................... B09C 1/10 210/606 |
| 2012/0258853 A1* | 10/2012 | Veeraraghavan ......... C09C 1/56 502/62 |
| 2016/0106635 A1* | 4/2016 | Yan ..................... C11D 11/0017 424/401 |

\* cited by examiner

*Primary Examiner* — Adam Marcetich
*Assistant Examiner* — Jessica R Arble
(74) *Attorney, Agent, or Firm* — Jeffrey L. Streets

(57) ABSTRACT

An absorbent pad includes a batt of cellulose fibers, superabsorbent particles intermixed within the batt of cellulose fibers, and an odor control material intermixed within the batt of cellulose fibers, wherein the odor control material is a particulate material including one or more fatty acid. The odor control material preferably further includes selected inorganic compounds, such as sources of nitrogen, phosphorus and iron. Various embodiments incorporate the absorbent pad in a diaper or other disposable hygiene product.

14 Claims, No Drawings

ABSORBENT PAD THAT INCLUDES A FATTY ACID COMPOSITION FOR ODOR CONTROL

CROSS-REFERENCE TO RELATED APPLICATIONS

This application claims the benefit of U.S. Provisional Application No. 62/269,282 filed on Dec. 18, 2015, which application is incorporated by reference herein.

BACKGROUND OF THE INVENTION

Field of the Invention

This invention relates to an absorbent pad, such as a diaper, including an odor control material.

Background of the Related Art

Disposable diapers are produced in a continuous process similar to an assembly line and can run at speeds of up to 1200 feet per minute and produce around 1000 diapers per minute. The process starts at the hammer-mill, where a sheet of pulp board is fed into a rotary hammer-mill and is converted into individual cellulose fibers (from 2.0 to 2.7 mm in length). These fibers are transported via an air stream into a forming drum made of individualized or continuous perforated screen pockets having a vacuum underneath to dissipate the air thus forming a cellulose batt of fibers. The drum former usually holds between 8 to 12 pockets (or individual diaper lengths), depending on diaper size and the diameter of the drum.

As these cellulose fibers are produced, they are mixed with a super-absorbent within the drum former. The super-absorbent particles (SAP) are measured by either gravimetric or volumetric feeders. The flow rate of these particles is controlled with great accuracy and the SAP is then fed into an airstream and combined in an admixture with the cellulose fibers prior to being formed into an absorbent batt in the drum former.

An odor control material (OCM) can be added to the absorbent core with a similar secondary apparatus, or combined with the SAP to form only one stream. The air forming technology used in the drum formers will allow either the OCM particles or the SAP to be strategically placed in the batt of fibers in either the X-Y plane, in the Z direction, or have them homogeneously mixed with the cellulose fibers.

The mix of cellulose fibers, SAP, and OCM being formed in the drum is called "the absorbent core". Once the pad is formed, a layer of tissue or light weight spunbond nonwoven is placed on the top, bottom or around the whole pad. A special adhesive can be used to adhere these layers to the absorbent core. This adhesive and the nonwoven provide integrity to the absorbent core and assist in containing the SAP and the OCM from coming out of the absorbent core during the process and while in use. The pad is then compressed using a de-bulking roll, or embossed with an embossing patterned roll.

In the next process steps, a polyethylene film or nonwoven film laminate is added at the bottom of the pad to provide the backsheet, and a non-woven material is added on top to provide the topsheet material or liner which is next to the skin. Spandex filaments of elastic are added at the edges of this structure in between the backsheet and topsheet to provide the leg elastic components. Then the leg cuff nonwoven material with additional Spandex filaments are added to the edges of the diaper on top of the topsheet to provide this containment feature. This composite structure is called the diaper "sausage".

A film frontal tape or nonwoven loop target material is adhered to the polyethylene film or nonwoven film laminate backsheet, using a cut and place applicator. Fastening tapes made with either positioning adhesive or with mechanical fasteners are added to the backsheet. In order to adhere all these materials, hot melt pressure sensitive adhesives (PSA) are used in the form of individual lines, slot coating or melt-spray. Two different types of pressure sensitive adhesives are used: one designed for the elastic components, and one used for laminating and attaching the nonwoven components of the diaper.

These fastening devices can either be attached directly to the diaper "sausage" as described above, or pre-attached to elastomeric materials to comprise the stretch "ear" portion of the diaper. The elastomeric side panels or "ears" can be adhered via PSA's, or via ultrasonic thermal bonding of the materials the combined topsheet and backsheet portion of the diaper sausage.

All of the components that are added to the diaper are registered in the machine direction usually by a vision inspection system to guarantee the proper placement of the components onto the diaper "sausage".

The diaper "sausage" is then cut into individual diapers and bi-folded or tri-folded prior to being inserted into a vertical or horizontal stacker. Here it is counted into whatever number of diapers is to be inserted into a diaper bag, which is then sealed for packing into corrugated cartons.

SUMMARY OF THE INVENTION

One embodiment of the present invention provides an absorbent pad comprising a batt of cellulose fibers, superabsorbent particles intermixed within the batt of cellulose fibers, and an odor control material intermixed within the batt of cellulose fibers, wherein the odor control material is a particulate material including one or more fatty acid.

Another embodiment of the present invention provides a diaper comprising an absorbent pad, wherein the absorbent pad includes a batt of cellulose fibers, superabsorbent particles intermixed within the batt of cellulose fibers, and an odor control material intermixed within the batt of cellulose fibers, and wherein the odor control material is a particulate material including one or more fatty acid.

DETAILED DESCRIPTION

One embodiment of the present invention provides an absorbent pad comprising a batt of cellulose fibers, superabsorbent particles intermixed within the batt of cellulose fibers, and an odor control material intermixed within the batt of cellulose fibers, wherein the odor control material is a particulate material including one or more fatty acid.

The superabsorbent particles may be made with any superabsorbent composition, such as polyacrylic acid sodium salt, polyacrylamide copolymer, ethylene maleic anhydride copolymer, cross-linked carboxymethylcellulose, polyvinyl alcohol copolymers, cross-linked polyethylene oxide, and a starch grafted copolymer of polyacrylonitrile.

The absorbent pad may be used in various manners and applications, such as in the production of a diaper or other disposable hygiene product, such as adult incontinence underwear and sanitary napkins or other feminine hygiene products. The absorbent pad may be used in additional manners and applications that require both the absorption of moisture and odor control.

In one option, the absorbent pad may further include a layer of tissue or light weight spunbond non-woven material secured on at least one side of the batt of cellulose fibers using an adhesive. In another option, the absorbent pad may further include a nonporous film secured on one side of the batt of cellulose fibers. Other features, such as elastic bands and fasteners, may also be added in order to form a diaper or other disposable hygiene product.

The odor control material is intermixed within the batt of cellulose fibers in an amount that is effective to control odor. Accordingly, the amount of odor control material may vary according to how the absorbent pad is being used and the nature of the odorous material. For example, in the absorbent pad of a diaper, between 0.5 grams and 5 grams of the odor control material intermixed in the cellulose fiber batt may be sufficient to control odors.

The odor control material of the present invention includes one or more fatty acids. The term "fatty acid" includes both saturated and unsaturated fatty acids. The term "saturated fatty acid" means an organic acid, typically monobasic, of the general formula $C_nH_{2n+1}COOH$ derived from the saturated series of aliphatic hydrocarbons; examples are palmitic acid, stearic acid and oleic acid. The term "unsaturated fatty acid" means an organic acid similar to a saturated fatty acid, except that it is has more than one bond (for example, a double bond) between at least one pair of adjacent atoms, usually carbon.

The one or more fatty acid may be a combination of a saturated fatty acid and an unsaturated fatty acids. One specific combination includes a saturated fatty acid having from 12 to 22 carbon atoms and an unsaturated fatty acid having from 12 to 22 carbon atoms. Another specific combination includes both saturated and unsaturated fatty acids having from 16 to 20 carbon atoms. Because the unsaturated fatty acids tend to be in the liquid phase at room temperature, it is preferred to provide the combination of saturated and unsaturated fatty acids together to form a solid particulate at room temperature and that will remain a solid even at elevated ambient temperatures. In one option, the one or more fatty acids may include one or more saturated fatty acid selected from stearic acid, palmitic acid and mixtures thereof. In another option, the one or more fatty acids may include at least one unsaturated fatty acid selected from oleic acid, linoleic acid and mixtures thereof.

The one or more fatty acids form a biodegradable composition that may include a saturated fatty acid selected from stearic acid, palmitic acid and combinations thereof, and an unsaturated fatty acid selected from oleic acid, linoleic acid and combinations thereof. The odor control material of the present invention may be prepared with any ratio of saturated fatty acids and unsaturated fatty acids. It is preferred for the composition to have a sufficiently high melting temperature to allow the material to be stored without clumping together. The preferred ratio of oleic acid (or any of the unsaturated fatty acids) to the saturated fatty acids is between about 70:30 and about 30:70 by weight, most preferably between 60:40 and 40:60 by weight. The most preferred fatty acids have between 14 and 20 carbon atoms.

The odor control material may further comprise additives, such as at least 1 weight percent of an amine-substituted form of a fatty acid. Another example of an additive is between about 0.1 and about 2 weight percent of amorphous silica mixed with the solids of the composition to prevent clumping of the material.

In one embodiment, the odor control material includes the one or more fatty acid combined with various inorganic compounds, such as a source of nitrogen, a source of phosphorus, and a source of iron. For example, one mixture of inorganic compounds (the percentages here are based only on the weight of the inorganic compounds, excluding any fatty acids or anticaking agents, etc.) includes between about 80 and about 90 percent (%) by weight of a source of nitrogen selected from ammonium sulfate $(NH_4)_2SO_4$, urea and combinations thereof; between about 5 and about 8 percent (%) by weight of a source of phosphorus selected from potassium phosphate dibasic $(K_2HPO_4)$, potassium phosphate monobasic $(KH_2PO_4)$, calcium phosphate monobasic $(CaHPO_4)$, calcium phosphate dibasic $Ca(H_2PO_4)_2$, calcium phosphate tribasic $Ca_3(PO_4)_2$, urea phosphate, ammonium phosphate $NH_4H_2PO_4$ and combinations thereof; and between about 1 and about 2 percent (%) by weight of a source of iron selected from ferrous sulfate $(FeSO_4)$, ferrous sulfate heptahydrate $(FeSO_4*7H_2O)$ and combinations thereof.

A particularly preferred odor control material includes the following: (1) 85 wt. % ammonium sulfate $((NH_4)_2SO_4)$, (2) 5 wt. % superphosphate $(Ca(H_2PO_4)_2)$, (3) 1 wt. % ferrous sulfate, (4) 4.2 wt % oleic acid, (5) 2.8 wt % stearic acid, and (6) 2 wt. % synthetic amorphous silica as an anticaking agent (available as PERKASIL® from W.R. Grace and Company). After blending the inorganic compounds and grinding them to pass a Number 60 sieve (i.e., a particle size of less than 0.25 millimeters), the inorganic compounds were mixed with the fatty acid mixture that had been heated to 100° C. The mixing was performed by adding the inorganic compounds into a ribbon blender at 70 rpm and then spraying the heated fatty acid mixture over the inorganic compounds with continuous mixing. After an additional 10-15 minutes of blending, the anticaking agent was added and blended for another 10-15 minutes. Only the product that passed through a Number 20 sieve (i.e., a particle size of less than 0.84 millimeters) was used.

While a combination of fatty acids may simply be mixed together to form a solid, a liquid or slurry, preferred compositions and preferred methods of making the compositions as a solid particle or powder are described in U.S. Pat. Nos. 5,443,845, 5,725,885 or 6,277,279, and each of these patents are incorporated by reference into this application. In a suitable method of preparing the composition, the fatty acids are mixed together, heated to melting, for example at 100 degrees Celsius, then cooled to produce a homogenous solid mixture.

When applying the one or more fatty acids to coat or encapsulate the inorganic compounds, the one or more fatty acids may be re-melted, for example at 100 degrees Celsius, to achieve a smooth flowing liquid, then cooled to about 65 degrees C., so that the fatty acids will solidify quickly when applied to the other compounds. Accordingly, the particulate composite can be manufactured in at least two ways. Using a conventional manufacturing method, the fatty acid component is added as a liquid into the dry solids mixer while the inorganic compounds are being blended. An appropriate dry solids mixer for this method is a ribbon blender (available from Ross Manufacturing). It may be helpful to equip the ribbon blender with a chopper attachment to reduce clumps that form in the mixing process. In one embodiment, the one or more fatty acids are added to inorganic compounds at a ratio of 10% by weight to ensure adequate encapsulation. The mixture of fatty acids and inorganic compounds must be removed from the mixer and passed through a U.S. standard number 20 sieve to remove clumped material. Preferably, the sifted material is then remixed with about 2% amorphous silica or any other standard anti-caking agent to maintain the free flowing properties of the particles. Whether or not inorganic compounds are included, the composition is preferably manufactured either as a powder, pellet or particulate of varying size.

Another embodiment of the present invention provides a diaper comprising an absorbent pad, wherein the absorbent pad includes a batt of cellulose fibers, superabsorbent particles intermixed within the batt of cellulose fibers, and an odor control material intermixed within the batt of cellulose fibers, and wherein the odor control material is a particulate material including one or more fatty acid.

The effectiveness of the odor control material in an absorbent pad is shown in the following examples.

Example 1

An odor control test was performed on absorbent pads made with and without the odor control material. The absorbent pads were manufactured using a cellulose batt that was formed from a mixture of cellulose fibers and a superabsorbent material. While one diaper was made as a control (i.e., the diaper included no odor control material), a second diaper was made further including 1 gram of an odor control material, and a third diaper was made further including 2 grams of the same odor control material. In the second and third diapers, the odor control material was mixed evenly in to the cellulose fibers and superabsorbent material before forming the adsorbent pad.

The odor control material included: (1) 85 wt. % ammonium sulfate (($NH_4)_2SO_4$), (2) 5 wt. % superphosphate ($Ca(H_2PO_4)_2$), (3) 1 wt. % ferrous sulfate, (4) 4.2 wt % oleic acid, (5) 2.8 wt % stearic acid, and (6) 2 wt. % synthetic amorphous silica as an anticaking agent (available as PERKASIL® from W.R. Grace and Company). After blending the inorganic compounds and grinding them to pass a Number 60 sieve (i.e., a particle size of less than 0.25 millimeters), the inorganic compounds were mixed with the fatty acid mixture that had been heated to 100° C. The mixing was performed by adding the inorganic compounds into a ribbon blender at 70 rpm and then spraying the heated fatty acid mixture over the inorganic compounds with continuous mixing. After an additional 10-15 minutes of blending, the anticaking agent was added and blended for another 10-15 minutes. Only the product that passed through a Number 20 sieve (i.e., a particle size of less than 0.84 millimeters) was used.

An equal amount of urine was applied to each of the three absorbent pads. The odor of each absorbent pad was measured after 3 hours, 4-6 hours, and 27 hours following the application of the urine.

TABLE 1

Odor Control Test Results

| Test Material Code | Amount of OCM (grams) | Odor After 3 Hours | Odor After 4-6 Hours | Odor After 27 Hours |
|---|---|---|---|---|
| 1 | 1 | 3 | 3 | 6 |
| 2 | 0 | 9 | 9 | 9 |
| 3 | 2 | 4 | 2 | 4 |

The odor scoring was on a scale from 0 (no odor) to 10 measured using a Hercules electronic nose at Alpha M.O.S. America of Hanover, Md. The Hercules electronic nose uses fast gas chromatography with an embedded pre-concentration trap, two capillary columns of different polarities (MXT-5 and MXT-1701) in parallel with a max temperature 280° C. and heating rates up to 5° C./s, and two flame ionization detectors.

Both of the two absorbent pads that included the odor control material were shown to be effective at reducing the odor, relative to the control. On average, the absorbent pad having the higher concentration (2 grams) of odor control material exhibited less odor than the absorbent pad having the lower concentration (1 gram).

The terms "comprising," "including," and "having," as used in the claims and specification herein, shall be considered as indicating an open group that may include other elements not specified. The term "consisting essentially of," as used in the claims and specification herein, shall be considered as indicating a partially open group that may include other elements not specified, so long as those other elements do not materially alter the basic and novel characteristics of the claimed invention. The terms "a," "an," and the singular forms of words shall be taken to include the plural form of the same words, such that the terms mean that one or more of something is provided. For example, the phrase "a solution comprising a phosphorus-containing compound" should be read to describe a solution having one or more phosphorus-containing compound. The term "one" or "single" shall be used to indicate that one and only one of something is intended. Similarly, other specific integer values, such as "two," are used when a specific number of things is intended. The terms "preferably," "preferred," "prefer," "optionally," "may," and similar terms are used to indicate that an item, condition or step being referred to is an optional (not required) feature of the invention.

It should be understood from the foregoing description that various modifications and changes may be made in the preferred embodiments of the present invention without departing from its true spirit. Accordingly, the foregoing description is for purposes of illustration only and should not be construed in a limiting sense. Only the language of the following claims should limit the scope of this invention.

What is claimed is:
1. An absorbent pad, comprising:
   a batt of cellulose fibers;
   superabsorbent particles intermixed within the batt of cellulose fibers; and
   an odor control material intermixed within the batt of cellulose fibers, wherein the odor control material is a particulate material that is a composite of one or more fatty acids mixed with a source of nitrogen, a source of phosphorus, and a source of iron.
2. The absorbent pad of claim 1, wherein between 0.5 grams and 5 grams of the odor control material is intermixed into between 6 and 16 grams of the cellulose fibers.
3. The absorbent pad of claim 1, further comprising:
   a layer of tissue or light weight spunbond non-woven material is secured on at least one side of the batt of cellulose fibers using an adhesive.
4. The absorbent pad of claim 3, further comprising:
   a nonporous film secured on one side of the batt of cellulose fibers.
5. The absorbent pad of claim 1, wherein the source of nitrogen is selected from ammonium sulfate $(NH_4)_2SO_4$, urea and combinations thereof;
   wherein the source of phosphorus is selected from potassium phosphate dibasic ($K_2HPO_4$), potassium phosphate monobasic ($KH_2PO_4$), calcium phosphate monobasic ($CaHPO_4$), calcium phosphate dibasic ($Ca(H_2PO_4)_2$), calcium phosphate tribasic ($Ca_3(PO_4)_2$), urea phosphate, ammonium phosphate ($NH_4H_2PO_4$), or combinations thereof; and wherein the source of iron is selected from ferrous sulfate ($FeSO_4$), ferrous sulfate heptahydrate ($FeSO_4 * _7H_2O$), or combinations thereof.

6. The absorbent pad of claim 1, wherein the one or more fatty acids include one or more saturated fatty acids selected from stearic acid, palmitic acid and mixtures thereof.

7. The absorbent pad of claim 1, wherein the one or more fatty acids include at least one unsaturated fatty acid selected from oleic acid, linoleic acid and mixtures thereof.

8. The absorbent pad of claim 1, wherein the one or more fatty acids include a saturated fatty acid and an unsaturated fatty acid, and wherein the ratio of the saturated fatty acid to the unsaturated fatty acid is between 70:30 and 30:70 by weight.

9. The absorbent pad of claim 8, wherein the saturated fatty acid includes stearic acid and the unsaturated fatty acid includes oleic acid.

10. The absorbent pad of claim 8, wherein the saturated fatty acid is stearic acid and the unsaturated fatty acid is selected from oleic acid, linoleic acid, and combinations thereof.

11. A diaper comprising the absorbent pad of claim 1.

12. An absorbent pad, comprising:

a batt of cellulose fibers;

superabsorbent particles intermixed within the batt of cellulose fibers; and an odor control material intermixed within the batt of cellulose fibers, wherein the odor control material is a particulate material including one or more fatty acids, wherein the one or more fatty acids include a saturated fatty acid and an unsaturated fatty acid, and wherein the ratio of the saturated fatty acid to the unsaturated fatty acid is between 70:30 and 30:70 by weight.

13. The absorbent pad of claim 12, wherein the saturated fatty acid includes stearic acid and the unsaturated fatty acid includes oleic acid.

14. The absorbent pad of claim 12, wherein the saturated fatty acid is stearic acid and the unsaturated fatty acid is selected from oleic acid, linoleic acid, and combinations thereof.

* * * * *